United States Patent [19]
Dongara et al.

[11] Patent Number: 5,677,260
[45] Date of Patent: Oct. 14, 1997

[54] CATALYST COMPOSITE FOR DEHYDROGENATION OF PARAFFINS TO MONO-OLEFINS AND METHOD FOR THE PREPARATION THEREOF

[75] Inventors: Rajeshwer Dongara; Arun Gurudath Basrur; Dattatraya Tammannashastri Gokak; Karumanchi Venkateshwara Rao; Konda Ramaswamy Krishnamurthy; Ishwar Singh Bhardwaj, all of Gujarat, India

[73] Assignee: Indian Petrochemicals Corporation Limited, Gujarat, India

[21] Appl. No.: 494,313

[22] Filed: Jun. 23, 1995

[51] Int. Cl.$^6$ .............................. B01J 23/32; B01J 23/72
[52] U.S. Cl. .............. 502/339; 502/325; 502/326; 502/327; 502/328; 502/332; 502/334; 502/336; 502/338; 502/340; 502/341; 502/349; 502/352; 502/355; 502/339; 585/660
[58] Field of Search .............................. 502/325, 326, 502/327, 328, 332, 334, 336, 338, 339, 340, 341, 349, 352, 355; 585/660

[56] References Cited

U.S. PATENT DOCUMENTS

| | | | |
|---|---|---|---|
| 3,632,661 | 1/1972 | Matzner | 260/683.3 |
| 3,892,657 | 7/1975 | Wilhelm | 208/139 |
| 3,915,868 | 10/1975 | Wilhelm | 252/466 |
| 4,078,743 | 3/1978 | Kogan | 252/442 |
| 4,136,064 | 1/1979 | Hayes | 252/466 |
| 4,197,416 | 4/1980 | Antos | 585/379 |
| 4,608,360 | 8/1986 | Abrevaya et al. | 502/226 |
| 4,786,625 | 11/1988 | Imai et al. | 502/326 |

FOREIGN PATENT DOCUMENTS 0183861  6/1986  European Pat. Off. .

*Primary Examiner*—Thurman K. Page
*Assistant Examiner*—Kathryne E. Shelborne
*Attorney, Agent, or Firm*—Ladas & Parry

[57] ABSTRACT

A novel catalyst composite for use in the dehydrogenation of paraffins to the corresponding monoolefins said composite incorporating within its spatial geometry on a percentage by weight basis a predetermined concentration gradient of a noble metal, a metal of Group IV A, a metal of Group III A, an alkali or alkaline earth metal element, a halogen; and a metal of Group VIII selected from, Fe, Co and Ni provided on a high surface area mesoporous support and a process for the preparation thereof.

29 Claims, 7 Drawing Sheets

CATALYST COMPOSITE FOR DEHYDROGENATION OF PARAFFINS TO MONO-OLEFINS AND METHOD FOR THE PREPARATION THEREOF

BACKGROUND OF THE INVENTION FIELD OF THE INVENTION

The present invention relates to a novel catalytic composite useful in the dehydrogenation of normal paraffins to the respective monoolefins and to a method for the preparation thereof. More specifically, the invention relates to a catalyst composite exhibiting high activity, stability and selectivity wherein the active elements are deposited in a pre-determined manner within the spatial geometry of the carrier therefor.

DESCRIPTION OF THE INVENTION

Dehydrogenation of paraffins, specifically $C_2$–$C_{20}$ paraffins, is an important petrochemical process through which a number of products useful in day to day life, such as plastics, synthetic rubber and detergents are manufactured. Furthermore, dehydrogenation of naphthenes and paraffins are the most facile reactions during catalytic reforming processes, practiced worldwide, for the production of aromatics (BTX) and high octane gasoline.

The dehydrogenation of n-paraffins especially in the range $C_{10}$ to $C_{16}$ is a reaction of prime importance particularly to the detergent industry for the manufacture of detergents. The dehydrogenation comprises a series of complex reactions involving parallel reactions accompanied by cracking, isomerization and coking reactions. The desired product is n-monoolefin which is formed in the first step of this series of reactions. Hence, selectivity is of paramount consideration. At the same time, there is a drawback: the life of most dehydrogenation catalysts is relatively short.

Towards maximizing selectivity and increasing catalyst life-span, it is conventional to attempt to suppress accompanying reactions by thermodynamically limiting per pass conversion by the application of pressure. However, it is the overall performance in terms of activity, selectivity and stability as exhibited by the catalyst that actually dictates the optimum feasibility of this reaction. This activity can be defined in terms of extent of per pass conversion as "the moles of paraffin converted per mole of paraffin fed", in terms of selectivity as "moles of n-monoolefin formed per mole of paraffin converted" and in terms of stability as "duration for which required activity and selectivity are maintained during the course of the reaction". Hence, it is the chemical components employed and the method of preparation of the catalytic composite which are responsible for any unique physico-chemical properties in the catalyst which enable it to evince these virtues. Catalyst preparation thus plays a key role.

Most catalytic compositions used to date for the dehydrogenation of paraffins consist of the following metals or combinations thereof, supported on a suitable porous, high surface area support such as gamma $Al_2O_3$:

1. Noble metal (Pt,Re,Pd,Ir,Au,Os).
2. Noble metal+Group IV A metal (Ge,Sn,Pb).
3. Noble metal+Group IV A metal+Group III A metal (Ga, In, Tl).
4. Noble metal+Other Group VIII metals, (Fe,Co,Ni) and/or alloys thereof.
5. 3 above+Group III A metal or Group III B metal (Sc,Y,La,Ac) as primary active agents, with Group II B metal (Zn,Cd,Hg) as optional secondary activating agents.
6. Noble metal+Group V A metal (As,Sb,Bi) or VI A element (S,Se,Te).
7. 1, 2, 3, 4, 5 or 6 above+Group VII A element, viz. halogen in combined form.
8. 1, 2, 3, 4, 5, 6, 7 above+Group I A metal or Group II A metal, viz. alkali or alkaline earth metals.
9. 1, 2, 3, 4, 5, 6, 7 or 8 above+Sulfur.

The references to Groups are based on the CAS version of the Periodic Table.

Indian Patent Specification No. 41,667 discloses a $Pt/Al_2O_3$ catalyst with combined halogen less than 8 weight percent calculated on an elemental basis suitable for dehydrogenation, reforming hydrogenation, hydrocracking and oxidation applications. U.S. Pat. Nos. 2,479,109 and 2,479,110 also disclose a catalyst of like composition.

U.S. Pat. No. 2,602,772 discloses addition of oxide of alkali metal or alkaline earth metal or Mg not exceeding 1 weight percent to a $Pt/Al_2O_3$ catalyst containing 0.1–8 weight percent combined halogen. The effect of Mg is reportedly lesser coke formation.

U.S. Pat. No. 2,930,763 discloses a catalyst composition consisting of Pt 0.1–1.0 weight percent, combined halogen (calculated on elemental basis) 0.1–1.0 weight percent, and alkali metal 0.01–1 weight percent for use in reforming applications in which dehydrogenation is one of predominant reactions.

Addition of elements of Group IV A or Group III A are disclosed in the following patents. U.S. Pat. No. 3,531,543 discloses a catalyst composition for dehydrogenation applications containing Pt, Sn, alkali metal and combined halogen, wherein the alkali metal is added to the support in a first step to yield a support like lithiated $Al_2O_3$. The purpose of alkali metal addition is to obtain a relatively neutral support.

U.S. Pat. No. 3,745,112 discloses a catalyst primarily for reforming applications of a similar composition to that disclosed in U.S. Pat. No. 3,531,543 wherein the role of the alkali metal is described as killing of the acidic function of the catalyst. Sn is described as a good promotor. U.S. Pat. No. 3,909,451 also describes a catalyst of similar composition for dehydrogenation wherein the combined halogen content, as calculated on an elemental basis, is less than 0.2 weight percent. Similarly, U.S. Pat. Nos. 4,329,258 and 4,363,721 describe catalysts containing Pt, Sn and an alkali metal and combined halogen wherein the atomic ratio of alkali metal to Pt is in the range 0.2 to 10.

U.S. Pat. No. 3,892,657 discloses a catalyst consisting of Pt, In and one of Ge, Sn or Pb along with combined halogen, the halogen content, as calculated on an elemental basis, varying from 0.1 weight percent for dehydrogenation application up to 3.5 weight percent for reforming applications and up to 10 weight percent for isomerisation applications. In is described as a good promotor when the atomic ratio of In: Pt is 0.1:1 to 1:1. A combination of Pt, Sn, In and Cl or Pt and one of Ge, Sn, Pb plus In is described as suitable for reforming reactions while a combination of Pt, In and alkali or alkaline earth metals is stated to be suitable for dehydrogenation. The combination of Pt, Sn, in and an alkali/ alkaline earth element is not specifically disclosed. Indian Patent Specification No. 128185 discloses a catalyst consisting of Pt, Ge and an alkali metal or alkaline earth metal on alumina for dehydrogenation applications. Indian Patent Specification No. 128349 describes a catalyst consisting of Pt, Sn and Ge on an alumina carrier. Indian Patent Specification No. 140805 discloses the addition of an alkali metal or alkaline earth metal in an amount of from 0.01–5 weight percent to a catalyst of composition as described in Indian Patent No. 128349 and shows the beneficial effect of this addition. The alkali/alkaline earth component is preferably added after impregnation of Pt, Sn and Ge.

Indian Patent Specification No. 145594 describes a catalyst composition consisting of Pt 0.2–1%, one of Ga, In,Tl, 0.2–1.0%, an alkali or alkaline earth element 0.2 to 2 weight percent and combined halogen 0.01 to 0.1 weight percent. This patent shows the superiority of such composition over prior art catalysts consisting of Pt/Al$_2$O$_3$ with alkali or alkaline earth elements with optionally, As or Pb as promotors. British Patent No. 1,499,297 discloses a catalyst similar in composition to that disclosed in Indian Patent Specification No.145594 for dehydrogenation applications wherein the alkali metal is preferably Li or K, and its atomic ratio in relation to Pt is up to 10 with combined halogen in the range 0.01–0.1 weight percent. Such composition is described as resulting in better selectivity and stability.

Indian Patent Specification No. 163412 also discloses a catalyst of composition similar to that disclosed in British Patent 1499 297 and Indian Patent Specification No. 145594. However, it claims that combined halogen content greater than 0.2% and an atomic ratio of alkali metal to Pt greater than 10 results in improved activity and selectivity.

Indian Patent Specification No. 165513 describes a catalytic composition consisting of Pt, one of Group IV A metal selected from Ge, Sn or Pb and an alkali or alkaline earth metal in an amount whereby the atomic ratio of this latter metal to Pt is greater than 10, and a combined halogen content exceeding 0.2 weight percent. Such composition is shown to exhibit better activity and selectivity than prior art catalysts with halogen content of less than 0.2 weight percent.

Indian Patent Specification No. 166585 discloses use of bifurcated alkali component such as a combination of Li and K to a catalyst of composition similar in other respects to that disclosed in Indian Patent Specification No. 165513.

Indian Patent Specification No.161974 discloses a catalyst for dehydrogenation applications consisting of Pt, Sn, In, an alkali or alkaline earth component and combined halogen, wherein the atomic ratio of In:Pt is greater than 1. The support is preferably an Sn—Al$_2$O$_3$ support. The patent discloses the promoting action of In. U.S. Pat. No. 3,632,661 discloses a catalyst consisting of Pt or Pd 0.1–5% along with Fe 0.01–10% or oxides/alloys thereof as promotors. The catalyst includes optionally Group I B metals as secondary promotors 0.002–5% or one of Co or Zn 0.1–4% with 0.2–2% weight percent alkali/alkaline earth metals on a near neutral carrier. The method avoids the use of halogenated salts for impregnation and preferably impregnates the promotor prior to the noble metal.

U.S. Pat. Nos. 2,814,599 and 2,914,464 describe catalysts containing one or more of Ga, In, So, Y, La, Tl and Ac as primary activating agents along with the optional addition of one or more of Hg, Zn or Cd as secondary activating agents for improved reforming activity.

Indian Patent Specification No. 136459 discloses a catalyst used in the dehydrogenation step, in the production of aryl substituted n-paraffins which consists of Pt 0.05–5 weight percent, an alkali or alkaline earth metal component such as Li 0.01–1.5 weight percent and one of Group V A or Group VI A elements, viz. As, Sb, Bi, S, Se, Te, preferably As, 0.01–1 weight percent.

SUMMARY OF THE INVENTION

The present invention discloses a novel catalyst composite which includes Fe along with Pt, Sn, In, Li and Cl. The novel catalyst composite of the present invention has better activity, selectivity and stability than the catalyst composites of the prior art and hence improves its overall performance in a reaction.

It is, therefore, the basic object of the present invention to provide a novel catalyst composite for use in the dehydrogenation of paraffins to monoolefins in Which the catalyst framework exhibits a predetermined distribution of the active elements within the spatial geometry of the catalyst particle.

A further object is the provision of a method for the preparation of such a catalyst composite which permits the distribution of active elements within the spatial geometry of the catalyst according to a pre-determined requirement.

Another object of the invention is to provide a catalyst having the ability to control within the spatial geometry of the catalyst frame work a desired distribution of the active elements of the catalyst.

DETAILED DESCRIPTION OF THE INVENTION

Accordingly, the present invention provides a novel catalyst composite for use in the dehydrogenation of paraffins to the corresponding monoolefins, said composite incorporating within its spatial geometry on a percentage by weight basis a predetermined concentration gradient of the following active elements:

from 0.1 to 5.0% of a noble metal;

from 0.1 to 5.0% of a metal of Group IV A;

from 0.1 to 6.0% of a metal of Group III A;

from 0.1 to 10.0% of an alkali or alkaline earth metal element;

from 0.01 to 10.0% of a halogen; and from 0.1 to 5.0% of a metal of Group VIII selected from Fe, Co and Ni provided on a high surface area mesoporous support.

According to a preferred embodiment, the catalyst composite of this invention consists of:

Platinum as the noble metal;

Tin (Sn) as the metal of Group IV A;

Indium (In) as the metal of Group III A;

Lithium (Li) as the alkali or alkaline earth metal element;

Chlorine (Cl) in combined form as the halogen; and

Iron (Fe) as the metal of Group VIII.

Preferably, Cl$^-$ is present in an amount of from 0.05% to 0.1% by weight calculated on an elemental basis and Fe is present in an amount of approximately 0.2% by weight.

The mesoporous support is preferably a spheroidal gamma alumina support having a diameter of 1.4 to 2.0 mm, a surface area in the range of from 120 to 250 m$^2$/g, a mesoporous pore distribution, a water adsorption capacity in the range of from 1.4 to 2.5 ml/g, a gamma crystallinity of from 60 to 80% and a bulk density of from 0.27 to 0.6 g/ml, preferably 0.3 gm/ml. Optionally the support also comprises 0.1–5.0 wt % Fe. In addition, the support should evince sound mechanical strength in terms of crush strength and loss on attrition.

The present invention also provides a process for the preparation of a novel catalyst composite incorporating a predetermined concentration gradient of active elements within its spatial geometry for use in the dehydrogenation of paraffins to the corresponding monoolefins which comprises incorporating on a percentage by weight basis within a high surface area mesoporous support:

from 0.1 to 5.0% of a noble metal;

from 0.1 to 5.0% of a metal of Group IV A;

from 0.1 to 6.0% of a metal of Group III A;

from 0.1 to 10.0% of an alkali or alkaline earth metal element;

from 0.01 to 10.0% of a halogen; and from 0.1 to 5.0% of a metal of Group VIII selected from Fe, Co and Ni drying the composite in which said active elements have been incorporated; and subjecting the dried composite to at least one calcination step.

According to the method of the present invention, the active elements can be incorporated simultaneously in combination into the mesoporous support in a single step or they may be incorporated stagewise employing any conventional procedure for the purpose. For instance, the active elements can be incorporated individually or in combination into the support during the preparation of the latter. Alternatively, such elements can be incorporated by impregnation of the finished support therewith, again individually or in combination.

In accordance with a specific embodiment, the noble metal, the metal of Group IV A, the metal of Group III A, the alkali or alkaline earth metal and the metal of Group VIII can be incorporated into an alumina support by co-precipitation or co-gellation during the sol state in the preparation of such support.

In an alternative embodiment, the metals identified can be impregnated into finished support. Such impregnation can be effected employing all the metals simultaneously or successively in any order.

For such impregnation, any conventional method may be employed such as equilibrium adsorption, incipient wetness, spraying, deposition as a film from the vapour state, co-precipitation, co-gellation or a combination of any of these. The choice of impregnation procedure will determine the formation of the desired concentration gradient of the active elements with the catalyst composite. The chosen procedure can also result in a composite having a heterogeneous or shell type deposition of elements therein or a homogeneous or uniform deposition of elements therein.

Preferably the noble metal, essentially platinum, is incorporated into the support simultaneously with the Group IV A metal, essentially tin.

Alternatively, the Group IV A metal is incorporated into the support in a separate step prior to incorporation of the other elements.

The Group III A metal, essentially indium, is preferably incorporated either simultaneously with or optionally after the Pt group (noble metal) has been incorporated into the support.

The alkali or alkaline earth metal, essentially lithium is preferably incorporated into the support prior to or simultaneously with the other elements.

Incorporation of the active elements into the finished support by impregnation is conveniently effected employing an aqueous solvent, an organic solvent or mixture of the two, in the presence of anions. Such anions are preferably acidic and in particular chloride anions in a concentration range from 0.1% to 15% by weight preferably 5% to 10% by weight. This range is maintained in order to achieve the desired distribution of active elements within the support framework for the catalyst.

In accordance with a preferred feature, the alumina support contains iron as the Group VIII metal which iron has been incorporated into the support at the sol stage of its preparation or in the first impregnation step.

Preparatory to impregnation, the aqueous and organic solutions employed for the purpose are preferably heated to a temperature of from 40° C. to 70° C. for a minimum of 30 minutes. Thereafter, the solutions are cooled to a temperature in the range of from 5° C. to 40° C. and maintained at this range during the impregnation step.

The quantum of the solution employed for impregnation by the incipient wetness technique is from 5% to 30% by weight in excess of the water adsorption capacity of the support measured according to IS 9700-1981.

The procedure found most convenient for incorporation of the active elements into the support is spraying of a solution of such elements on to the support at a controlled rate while rotating the support at a predetermined angle of inclination with respect to the spray. This procedure yields a catalyst with uniform dispersion of elements therein and ensures minimal loss of the impregnated support which would otherwise occur by mechanical fracture of the support as a result of the heat of adsorption of the impregnating solution.

After incorporation therein of the active elements, the catalyst composite is preferably dried in a dust-free environment at ambient temperature for from 0.5 to 6 hours and thereafter in a flow of purified air at a temperature from 80° C. to 170° C. for 4 to 12 hours.

The calcination of the dried catalyst composite can be effected in one or more stages at a temperature in the range of from 400° C. to 650° C. for a period of from 4 to 16 hours in an environment of circulating dry air.

According to a further feature of the invention, the calcined catalyst composite is subjected to dehalogenation treatment preferably by employing a counter current stream in order to reduce its halogen content to 0.01% to 5%, preferably 0.05% to 0.1%, by weight. The dehalogenated composite is then washed, dried and further calcined whereafter it is ready for use in the dehydrogenation of $C_{10}$ to $C_{14}$n-paraffins.

It has been found convenient to dehalogenate the catalyst composite by subjecting it to steaming employing a 20:80 steam-air mixture at a temperature of from 400° C. to 550° C.

Alternatively, the composite can be dehalogenated by treating it at a temperature of from 10° C. to 80° C. for a period of from 0.5 to 10 hours with an aqueous solution of a weak base or salt thereof or with an aqueous solution of an organic or inorganic compound which undergoes hydrolysis to release such weak base at the temperature mentioned. This alternative dehalogenation treatment is preferred and the preferred temperature thereof is 40° C. to 80° C.

A preferred washing medium for the dehalogenated composite is demineralized water with the washing effected at a temperature of 10° C. to 80° C. for a period of 0.5 to 5 hours. The drying and calcination are effected in the manner identified above.

The invention will be described in greater detail with reference to the accompanying drawings and examples that follow.

In such examples, unless otherwise specified, a chloride content of between 8 to 10 weight, percent is maintained in the impregnating solution whenever spraying is employed as the preferred manner of impregnation.

EXAMPLE - I

Preparation of Catalyst Composite of Formulation
A

The benefit of including Fe in the catalyst formulation.

Employing spray procedure in a two-step impregnation of a spheroidal alumina support, a catalyst composite according to the present invention was prepared having the following composition by weight:

| | |
|---|---|
| Pt | 0.4% |
| Fe | 0.2% |
| Sn | 0.5% |
| In | 0.4% |
| Li | 0.6% |
| Cl | 0.07% |

The alumina support employed had an average particle diameter of 1.85 mm with 68% gamma crystallinity, a BET surface area of 170 m²/g, a water adsorption capacity (WAC) of 1.8 ml/g, mesoporous distribution of pores, a bulk density of 0.31 g/ml, and a Fe content of 0.2 wt % as a solution of Fe [NO$_3$]$_3$ which was incorporated into the support at the sol stage in its preparation.

In the first step of impregnation, a solution of LiNO$_3$ was employed to impregnate the support whereafter the support thus impregnated was dried and calcined. Pt, Sn and In were impregnated in a second step by spraying it with a second solution containing H$_2$PtCl$_6$, SnCl$_2$, In[NO$_3$]$_3$ and HCl. The re-impregnated support was once again dried and calcined and then subjected to a de-halogenation step in order to reduce the chlorine content thereof to 0.07% by weight. This catalyst exhibits a monoolefin selectivity of 89–90%.

EXAMPLE - II

Preparation of Catalyst Composite of Formulation
B

Figure 1:
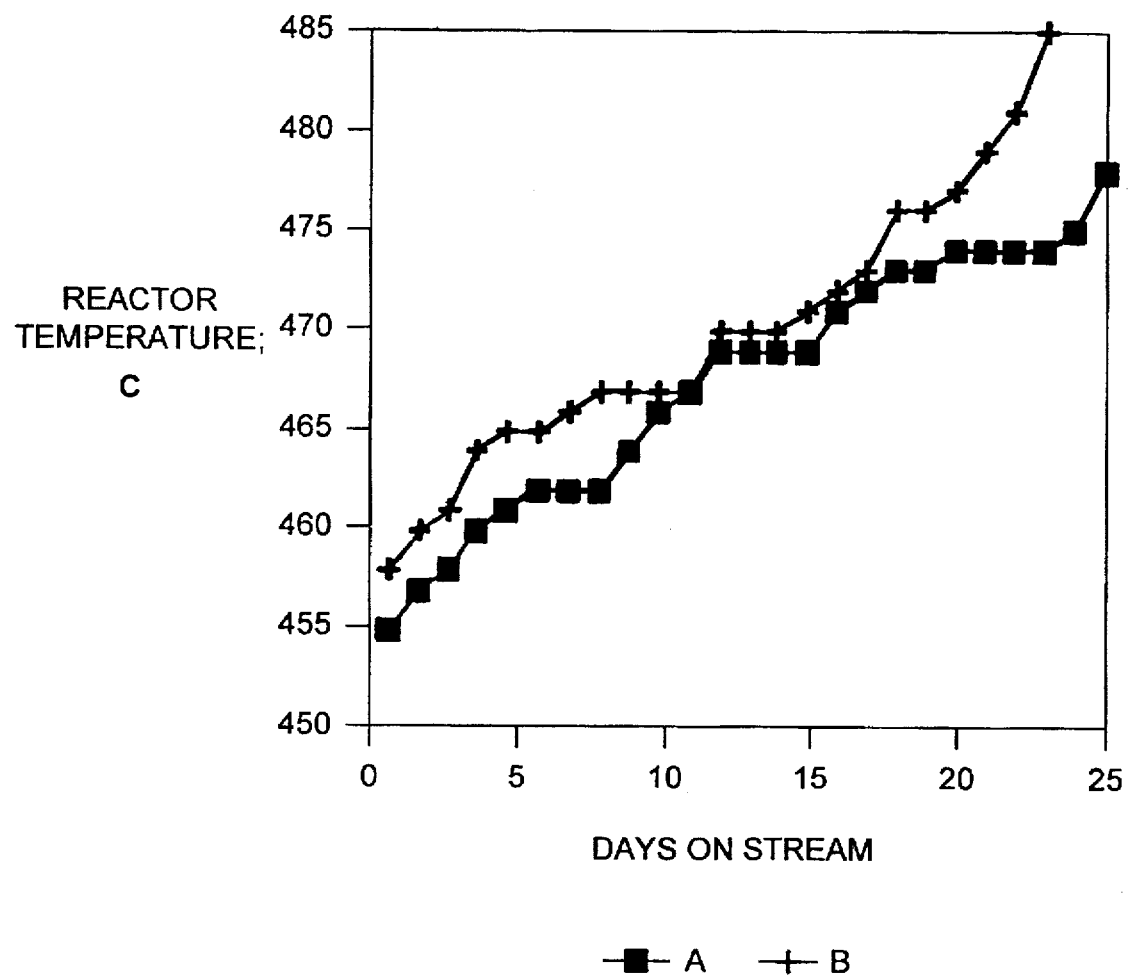
FIG. 1 Brings out the effect of Fe in the catalyst formulation.

Formulation B was prepared using the same support as for Formulation A the only difference being that Fe was not included in the formulation. The results are presented in FIG. 1. It is clear that incorporation of Fe increases both the activity [temperature for a given paraffin conversion is lower than in catalyst B] and stability [at 25 days on stream the reactor temperature is 10° C. lower than for catalyst B] of the catalyst.

EXAMPLE III

Preparation of Catalyst Composite of Formulation
C

The importance of addition of Pt and Sn together.

Catalysts of composition similar to that in Example I, Formulation A, were prepared by a different method of impregnation wherein Fe was incorporated at sol stage, then Sn and Li were impregnated onto the alumina support in a first step by spraying an aqueous mixture of SnCl$_2$ in 5% HCl and LiNO$_3$ onto the support as per the method described in this patent. This was followed by a drying and calcination step followed by incorporation of Pt and In together in a second step also by spraying of a mixture of the solutions of their salts as described in this patent. The catalyst was dried and calcined. It was then subjected to a dehalogenation step and the Cl⁻ content reduced to 0.08 wt. %.

The results of evaluation of this catalyst formulation via a vis Formulation A showed that the initial activity of both catalysts is identical but Formulation C tends to deactivate rapidly due to coking [fall in activity is about 1.25 times that of Formulation A]. The results show that incorporation of the other active elements, especially Sn, prior to incorporation of Pt results in relatively poor stability.

EXAMPLE IV

Preparation of Catalyst Composite of Formulation
D

Figure 3:
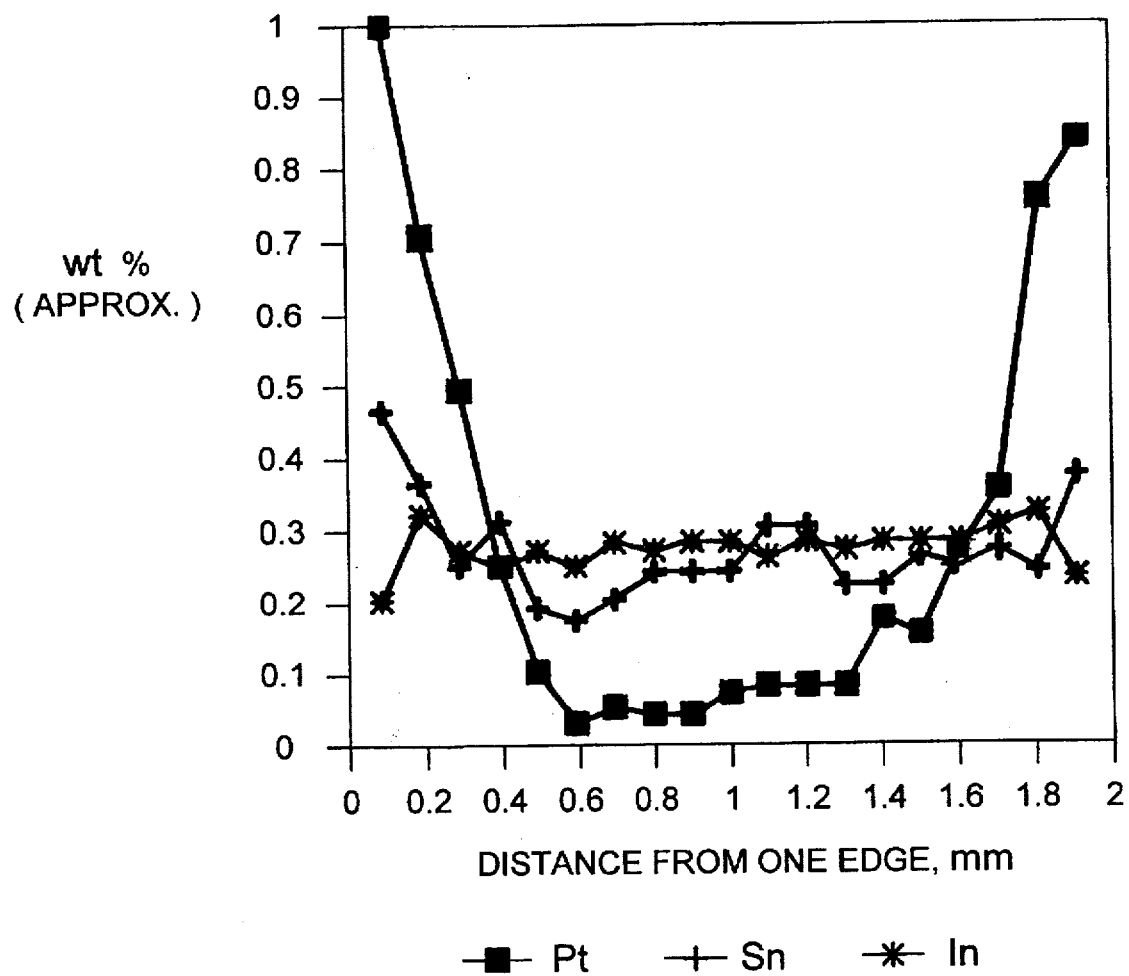
FIG. 3 Concentration profile of Pt, Sn, In, in Catalyst formulation D.

The support used was identical to that used in the case of formulation A. Final compositions too were similar. The method of impregnation however is two step, LI, Sn and In were incorporated in the first step by the spray method described in this patent. This was followed by drying and calcination prior to loading of Pt from a solution of H$_2$PtCl$_6$ by the equilibrium adsorption method wherein the solid/solution ratio was maintained at 1:7, additional Cl⁻ as HCl was not added to this solution. The contact time was 24 h, Pt uptake from solution was 99 weight percent. This was followed by drying and calcination. This formulation results in a shell type catalyst wherein Pt is restricted to an outer shell, approximately 300 nm thick, of the catalyst spheroid of average diameter 1.85 mm. The other active elements are uniformly distributed. The interior of the catalyst particle contains very little of Pt. The EDAX (Energy Dispersive Analysis Of X-Rays) results of the profiles of various active elements are shown in FIG. 3.

EXAMPLE V

Preparation of Catalyst Composite of Formulation
E

Formulation E is similar in composition to formulation D. In its method of preparation the steps of formulation D have been reversed. Pt as H$_2$PtCl$_6$, in aqueous HCl amounting to 1 wt. % Cl⁻, was incorporated in the first step by the equilibrium adsorption technique. The catalyst was dried and calcined. The other elements Sn, In, Li were added by spraying in a second step. Followed by drying, calcination and dehalogenation.

EXAMPLE VI

Preparation of Catalyst Composite of Formulation
F

Formulation F was prepared in a manner similar to formulation E, except that the other elements, Li, Sn and In were impregnated by spraying in a first step followed by drying and calcination. The Pt along with 1% Cl⁻ as HCl was incorporated by equilibrium adsorption in a second step. The catalyst was dried, calcined and dehalogenated by the preferred method as cited in this patent.

Figure 2:
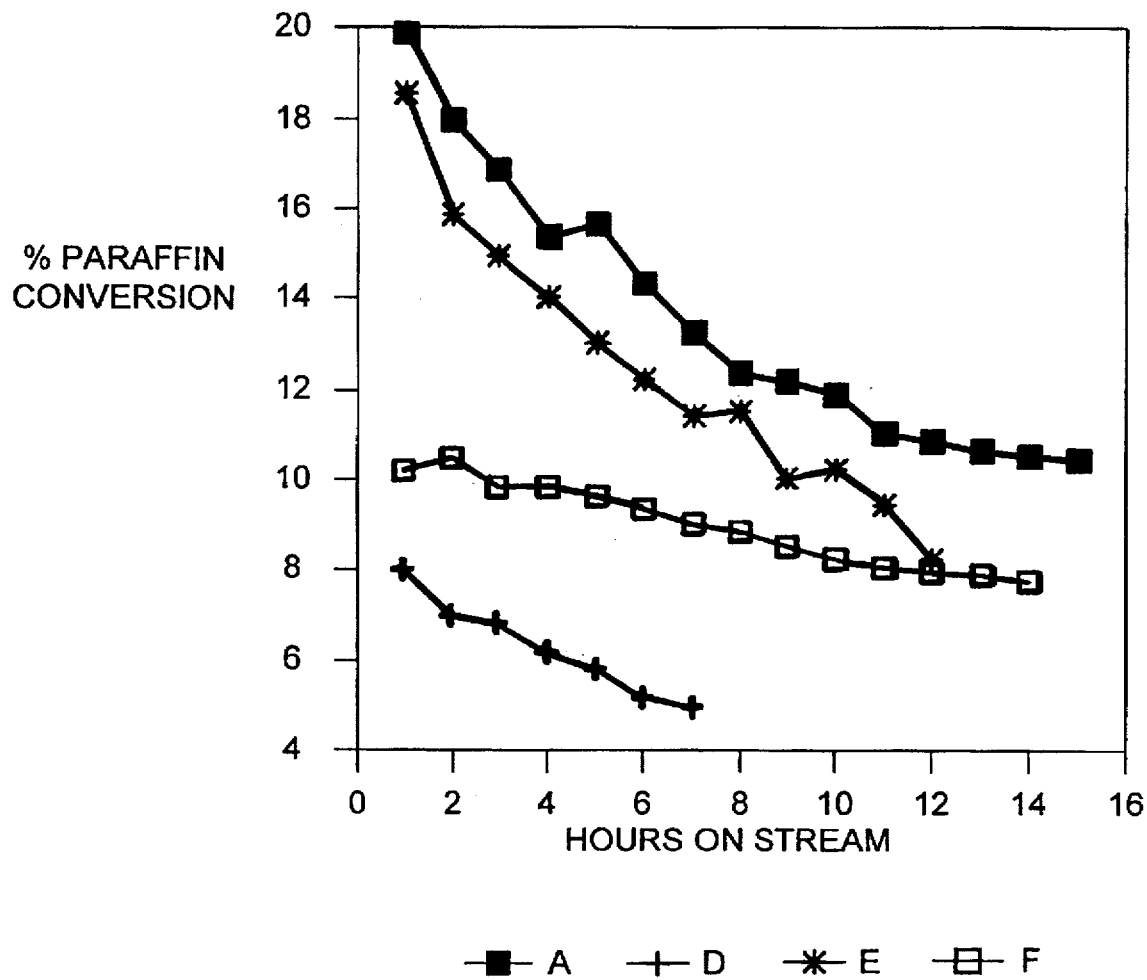
FIG. 2 Comparison of activities of catalyst formulation prepared.

Results of C$_{10}$–C$_{13}$ n-paraffin dehydrogenation over these two catalysts are presented in FIG. 2. The results for formulation A which is prepared by the preferred method as disclosed in this patent is also included in this figure for comparison. Catalyst formulation A is undoubtedly the superior of the four followed by E. The performance of formulations F and in particular D is poor. These catalysts were prepared by addition of Sn, In and Li to $Al_2O_3$ by spraying and incorporating Pt in a second step by equilibrium adsorption method. The subtle difference between the latter two is the chloride content of the impregnating solution. In the case of formulation D additional Cl⁻ in the form of HCl was not added to the impregnating solution whereas in case of F, 1 weight percent of Cl⁻ was added as HCl. In spite of its poor catalytic activity the method of preparation of formulation D in particular, provides a means for distribution of the active element/s viz. Pt selectively in the shell region as shown in FIG. 3.

EXAMPLE VII

Preparation of Catalyst Composite of Formulations G, H, I, J, K, L

Figure 4A:
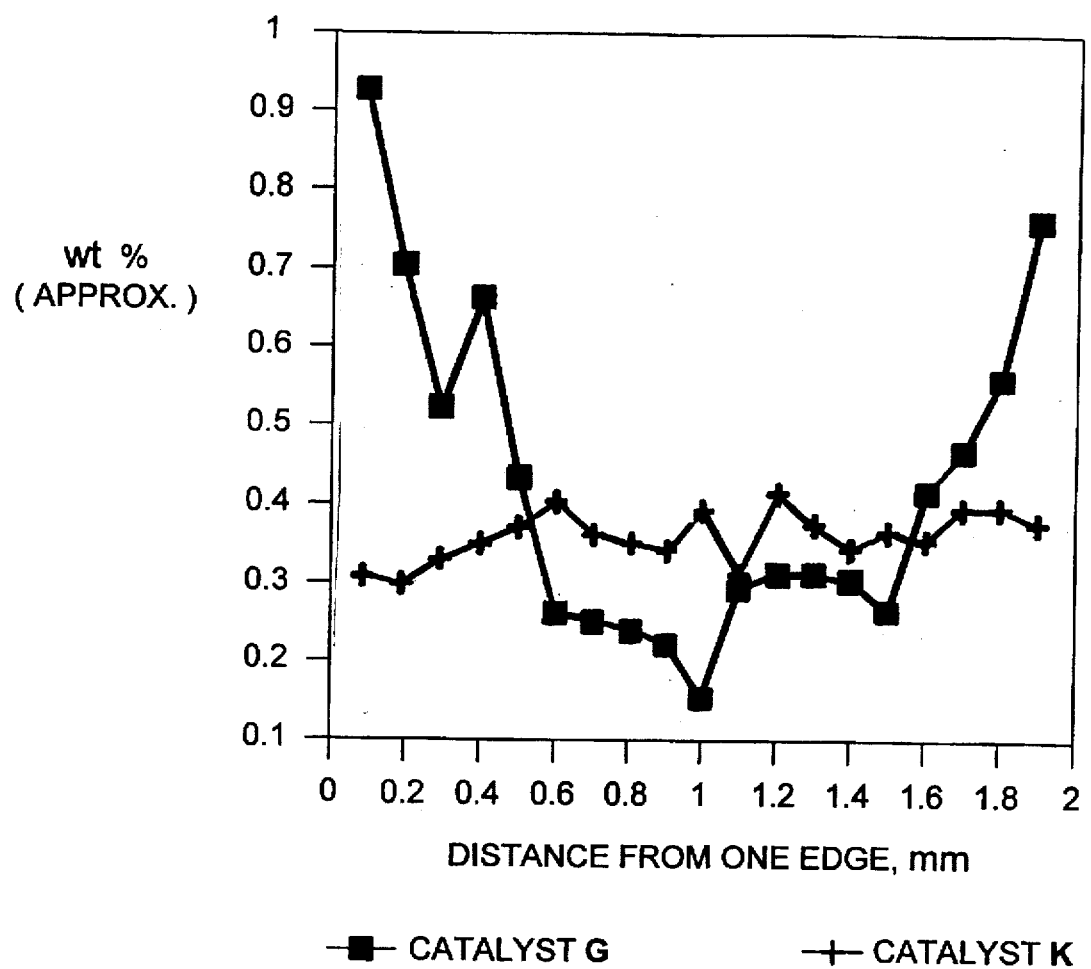
FIG. 4a Effect of Cl on concentration profile of Sn in catalysts prepared by incepient wetness.
Figure 4B:
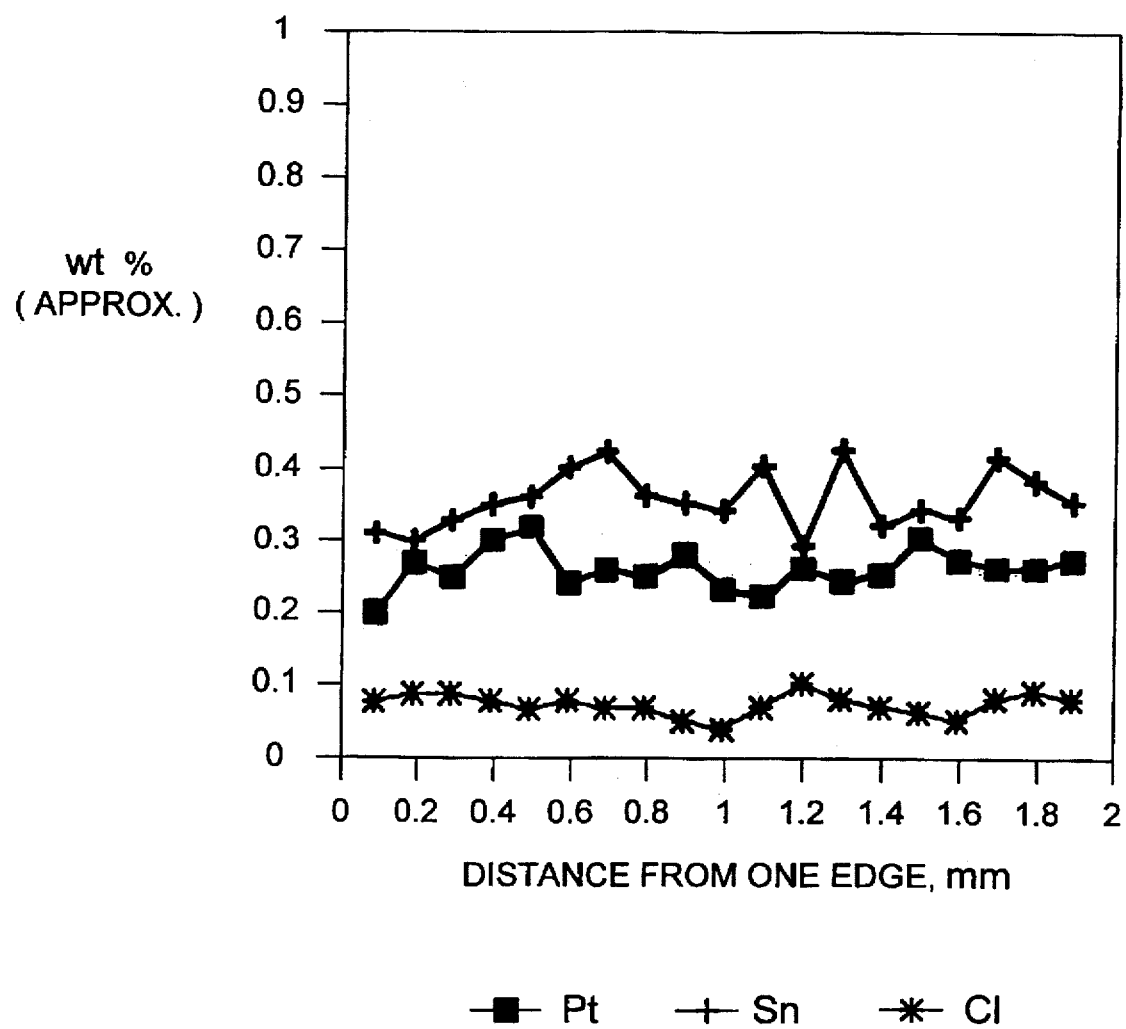
FIG. 4b Effect of Cl content and method of impregnation on concentration profile of Pt, Sn and Cl.
Figure 4C:
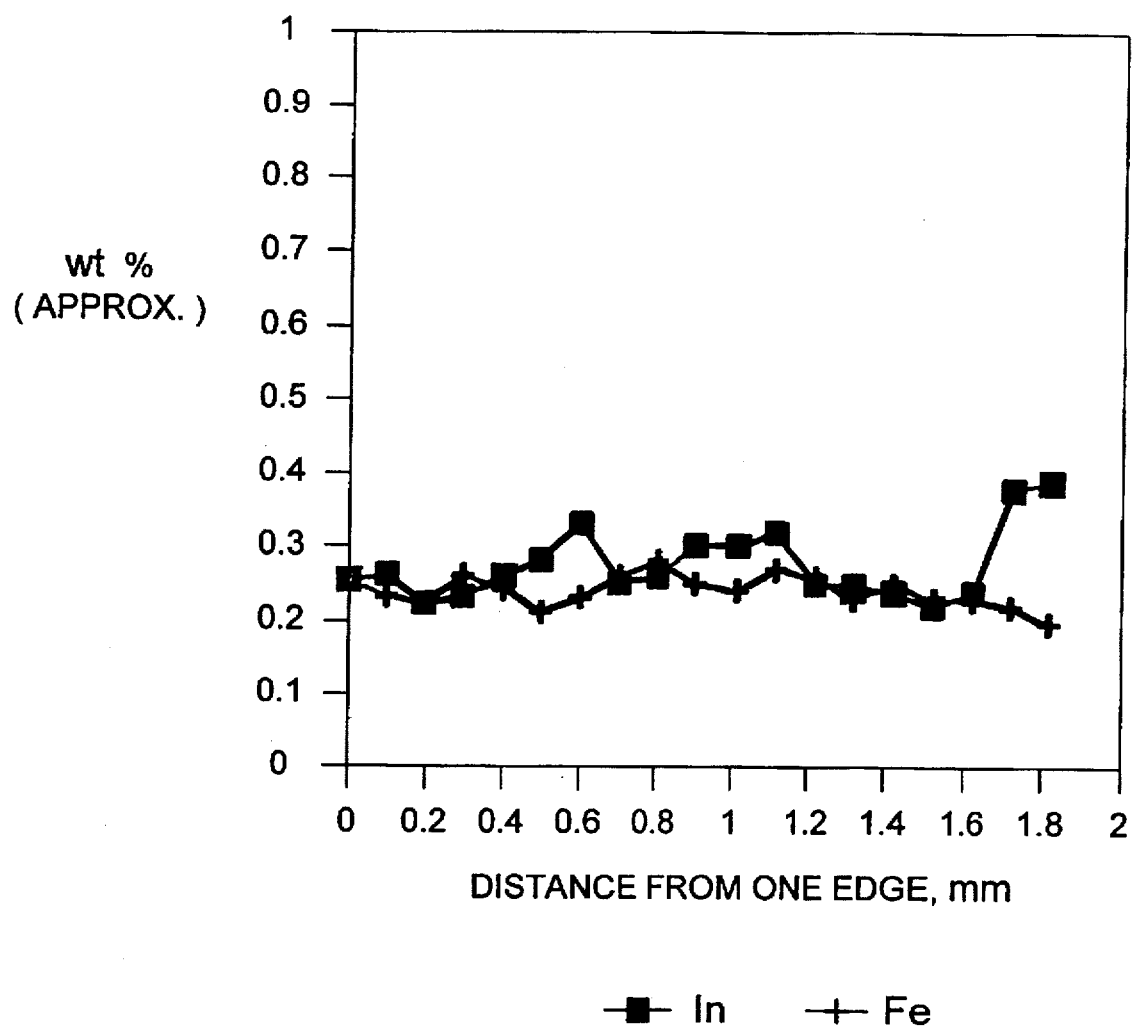
FIG. 4c. Effect of Cl content of impregnating solution on concentration profile of In and Fe.

The alumina support was the same as that used for formulation A. These catalysts were prepared by the single step impregnation method (spraying) wherein the solution impregnated was a mixture of the solutions of all the active elements. The difference between these formulations was the quantity of acid anion Cl⁻ in the impregnating solution. This factor was varied by addition of HCl acid where required to maintain higher Cl⁻ concentration. The concentrations of this anion in the impregnating solution were, in the same order, 1, 3, 5, 7, 9 and 11 wt. %. The typical concentration profiles for Sn across the diameter of the catalyst sphere as determined by EDAX analysis are presented in FIG. 4a. The results show that the distribution of Sn within the spatial geometry of the catalyst particle is affected by the quantity of Cl used in the impregnating solution. A minimum Cl content of 9 wt. % in the impregnating solution, is required for uniform distribution of Sn. Lower Cl content leads to higher concentration of Sn towards the shell of the spheroid. The other active elements are distributed uniformly. Typical EDAX concentration profiles for these are shown in FIG. 4b, for Pt, Sn and Cl and in FIG. 4c for In and Fe.

From Examples III and IV, it is seen that by judicious selection of the method of impregnation as well as by adjustment of the content of competing anion in the impregnating solution, the active metals can be distributed either uniformly or heterogeneously onto the support.

EXAMPLE VIII

Figure 5:
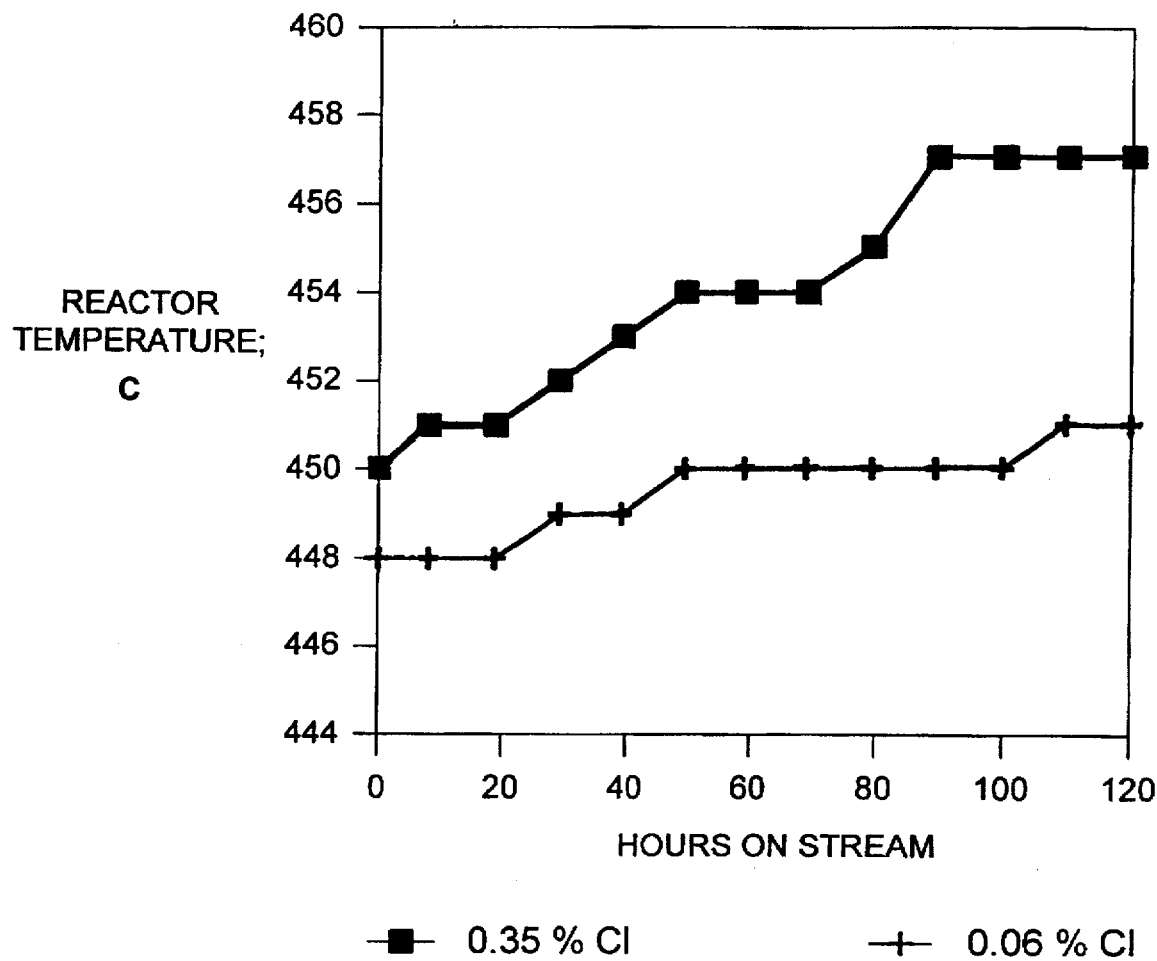
FIG. 5 Effect of residual Cl content of catalyst on stability.

The effect of the quantity of residual acidic anion in the catalyst is shown through this example. The catalyst was prepared by the preferred method viz. two step impregnation. Hence, the formulation is essentially the same as that of A. The difference is in the residual chloride content of the catalyst. In one catalyst the residual chloride content is 0.35 wt. %, whereas in another it is 0.06 wt. %. The results of performance of these catalysts for the dehydrogenation of $C_{10}-C_{13}$ n-paraffins is presented in FIG. 5. The results clearly show an inverse relation between stability and chloride content.

From the examples, it is clear that the invention enables the achievement of three distinctly different distributions of the active elements within the spatial geometry of the catalyst particle. For example, Formulation B of Example II exhibits uniform distribution of all the active elements FIG. 4b, 4c. Formulation C of Example III exhibits restriction of Pt to only the shell region while the other active elements are uniformly distributed in the catalyst spheroid FIG. 3. Formulations G to L of Example VII show a trend in the distribution of Sn with Increasing Cl⁻ content of the impregnation solution [FIG. 4a] therein. Thus, the present invention succeeds In establishing a method for obtaining a desired distribution of active elements within the catalyst particle.

Certain catalyst formulations prepared according to the present invention were tested for their activity, stability and selectivity for dehydrogenation of $C_{10}-C_{13}$ n-paraffins under the reaction conditions described hereafter. All experimental tests were performed in a once-through, tubular, axial flow, packed bed reactor operated at near isothermal conditions. The catalysts were reduced in a stream of hydrogen at 470° C. for 2 hours in all the cases.

Essentially, two types of tests were carried out as follows:

Isothermal Tests: Monitoring of conversion of the paraffins under near isothermal reaction conditions. Specifically, the reaction conditions were:

LHSV: 30 h⁻¹,

Temperature: 450° C.,

Pressure: atmospheric, $H_2$:HC (mol/mol): 6.

Isoconversional Tests: Monitoring of the reactor temperature required for operating the reactor at a constant level of paraffin conversion viz 13% per pass conversion. The reaction conditions were:

LHSV: 20 h⁻¹

Pressure: 20 psi $H_2$:HC (mol/mol): 6

Conversion level: 13±0.5%.

As stated earlier, "conversion" is defined as "the moles of paraffin converted per mole of paraffin fed" and "selectivity" is defined as "the parts of monoolefins formed per part of paraffin converted across the reactor".

The scope of the patent is not restricted only to the examples as given above and covers the various methods and active species as have been described in this patent.

We claim:

1. A catalyst composite for use in the dehydrogenation of paraffins to the corresponding monoolefins said composite incorporating within its spatial geometry on a percentage by weight basis a predetermined concentration gradient of the following active elements:

from 0.1 to 5.0% of a noble metal;

from 0.1 to 5.0% of a metal of Group IV A;

from 0.1 to 6.0% of a metal of Group III A;

from 0.1 to 10.0% of an alkali or alkaline earth metal element;

from 0.01 to 10.0% of a halogen; and from 0.1 to 5.0% of a metal of Group VIII selected from Fe, Co and Ni provided on a high surface area mesoporous support.

2. A catalyst as claimed in claim 1 wherein the catalyst composite consists of the following as active elements:

Platinum as the noble metal;

Tin (Sn) as the metal of Group IV A;

Indium (In) as the metal of Group III A;

Lithium (Li) as the alkali or alkaline earth metal element;

Chlorine (Cl) in combined form as the halogen; and

Iron (Fe) as the metal of Group VIII.

3. A catalyst as claimed in claim 2 wherein chlorine is present in an amount from 0.05% to 0.1% by weight and Fe is present in an amount of 0.2% by weight.

4. A catalyst as claimed in claim 2 wherein the mesoporous support is a spheroidal gamma alumina support having a diameter of 1.4 to 2.0 mm., a surface area in the range of 120 to 250 m²/g, a mesoporous pore distribution, a water adsorption capacity in the range of from 1.4 to 2.5 ml/g, a gamma crystallinity of from 60 to 80% and a bulk density of from 0.27 to 0.6 gm/ml.

5. A catalyst as claimed in claim 4 wherein the support also comprises 0.1 to 5.0 wt. % Fe.

6. A process for the preparation of a catalyst composite incorporating a predetermined concentration gradient of active elements within its spatial geometry for use in the dehydrogenation of paraffins to the corresponding monoolefins which comprises incorporating on a percentage by weight basis within a high surface area mesoporous support:
  from 0.1 to 5.0% of a noble metal;
  from 0.1 to 5.0% of a metal of Group IV A;
  from 0.1 to 6.0% of a metal of Group III A,
  from 0.1 to 10% of an alkali or alkaline earth metal element;
  from 0.01 to 10.0% of a halogen; and
  from 0.1 to 5.0% of a metal of Group VIII selected from Fe, Co and Ni, drying the composite in which said active elements have been incorporated; and
  subjecting the dried composite to at least calcination step, said mesoporous support being a spheroidal gamma alumina support having a diameter of 1.4 to 2.0 mm., a surface area in the range of 120 to 250 m²/g, a mesoporous pore distribution, a water adsorption capacity in the range of from 1.4 to 2.5 ml/g, a gamma crystallinity of from 60 to 80% and a bulk density of from 0.27 to 0.6 g/ml.

7. A process as claimed in claim 6 wherein the active elements are incorporated into the mesoporous support in a single step or stage wise.

8. A process as claimed in claim 7 wherein the active elements are incorporated individually or in combination into the support during the sol stage of preparation of said support.

9. A process as claimed in claim 7 wherein the active elements are incorporated individually or in combination by impregnation of the finished support therewith.

10. A process as claimed in claim 8 wherein Fe is incorporated during the sol stage of preparation of the support or by impregnation into the finished support before, during or after incorporation of the other elements.

11. A process as claimed in claim 8 wherein Sn component is incorporated at the sol stage of preparation of the support prior to, along with or after the other active elements are incorporated preferably along with Pt or to the finished support.

12. A process as claimed in claim 9 wherein In is incorporated at the sol stage of preparation of the support or by impregnation into the finished product either simultaneously with the other elements or singly but preferably not prior to incorporation of Pt.

13. A process as claimed in claim 9 wherein Pt is incorporated by impregnation of the support either simultaneously with other elements or singly but preferably not after In.

14. A process as claimed in claim 9 wherein Li is incorporated at the sol stage in the preparation of the support or simultaneously with other elements or singly during impregnation of the support but preferably not after incorporation of the other elements.

15. A process as claimed in claim 14 wherein the impregnation is effected by employing an aqueous solvent, an organic solvent or mixture of the two in the presence of anions.

16. A process as claimed in claim 15 wherein anion are acidic anions.

17. A process as claimed in claim 15 wherein the impregnating solution is heated to a temperature of from 40° to 70° C. for a minimum of 30 minutes, cooled to a temperature in the range of 5° C. to 40° C. and maintained at this temperature during impregnation.

18. A process as claimed in claim 17 wherein the volume of said impregnating solution is 5% to 30% in excess of the water adsorption capacity of the support.

19. A process as claimed in claim 6 wherein Pt content is either uniformly distributed or restricted to a narrow shell region within the catalyst spheroid.

20. A process as claimed in claim 6 whereby the distribution of Sn within the spatial geometry of the catalyst particle may be varied from restriction to the shell region to uniform distribution throughout the particle, by the control of chloride content of the impregnating solution.

21. A process for the preparation of a catalyst composite incorporating a predetermined concentration gradient of active elements within its spatial geometry for use in the dehydrogenation of paraffins to the corresponding monoolefins which comprises incorporating on a percentage by weight basis within a high surface area mesoporous support:
  from 0.1 to 5.0% of a noble metal;
  from 0.1 to 5.0% of a metal of Group IV A;
  from 0.1 to 6.0% of a metal of Group III A;
  from 0.1 to 10.0% of an alkali or alkaline earth metal element:
  from 0.01 to 10.0% of a halogen; and
  from 0.1 to 05.0% of a metal of Group VIII selected from Fe, Co and Ni drying the composite in which said active elements have been incorporated; and
  subjecting the dried composite to at least one calcination step;
  subjecting further the calcined composite to controlled treatment with a solution of a salt of a weak base which on hydrolysis at elevated temperature releases $NH_3$, or with a solution of $NH_4OH$ at between 40°–70° C. for 1 to 4 hours to decrease the chloride content to about 0.04 to 0.1 wt. %.

22. A catalyst as claimed in claim 2 wherein the mesoporous support is a spheroidal gamma alumina support having a diameter of 1.4 to 2.0 mm, a surface area in the range of 120 to 250 m²/g and a mesoporous pore distribution.

23. A catalyst as claimed in claim 2 wherein the mesoporous support is a spheroidal gamma alumina support having a water adsorption capacity in the range of from 1.4 to 2.5 ml/g.

24. A catalyst as claimed in claim 2 wherein the mesoporous support is a spheroidal gamma alumina support having a gamma crystallinity of from 60 to 80% and a bulk density of from 0.27 to 0.6 gm/ml.

25. A catalyst as claimed in claim 2 wherein the mesoporous support is a spheroidal gamma alumina support having a gamma crystallinity of from 60 to 80% and a bulk density of 0.3 gm/ml.

26. A catalyst as claimed in claim 4 wherein the bulk density of the mesoporous support is 0.3 gm/ml.

27. A process according to claim 6 wherein the bulk density of the mesoporous support is 0.3 gm/ml.

28. A catalyst as claimed in claim 16 wherein the acidic anions are chloride anions in the range of 0.1 to 15.0% by weight.

29. A catalyst as claimed in claim 16 wherein the acidic anions are chloride anions in the range of 8.0% to 10.0% by weight.

* * * * *